United States Patent
Castillo et al.

(10) Patent No.: US 12,157,879 B2
(45) Date of Patent: Dec. 3, 2024

(54) CELL CULTURE CLARIFICATION

(71) Applicant: EXOTHERA SA, Charleroi (BE)

(72) Inventors: José Castillo, Brussels (BE); Vasily Medvedev, Nivelles (BE)

(73) Assignee: EXOTHERA SA, Charleroi (BE)

( * ) Notice: Subject to any disclaimer, the term of this patent is extended or adjusted under 35 U.S.C. 154(b) by 1434 days.

(21) Appl. No.: 16/499,348

(22) PCT Filed: Mar. 30, 2018

(86) PCT No.: PCT/EP2018/058366
§ 371 (c)(1),
(2) Date: Sep. 30, 2019

(87) PCT Pub. No.: WO2018/178376
PCT Pub. Date: Oct. 4, 2018

(65) Prior Publication Data
US 2020/0056144 A1    Feb. 20, 2020

(30) Foreign Application Priority Data

Mar. 30, 2017  (BE) .................................. 2017/5210

(51) Int. Cl.
| | |
|---|---|
| C12M 1/00 | (2006.01) |
| B01D 15/38 | (2006.01) |
| B01D 37/02 | (2006.01) |
| B01J 20/14 | (2006.01) |
| C07K 16/00 | (2006.01) |
| C12M 1/06 | (2006.01) |

(Continued)

(52) U.S. Cl.
CPC ......... *C12M 47/12* (2013.01); *B01D 15/3809* (2013.01); *B01D 37/02* (2013.01);
(Continued)

(58) Field of Classification Search
None
See application file for complete search history.

(56) References Cited

U.S. PATENT DOCUMENTS 2,878,938 A * 3/1959 Chandler ............... B01D 37/02
210/167.13
5,369,011 A * 11/1994 Ebersole .......... G01N 33/56911
435/9
(Continued)

FOREIGN PATENT DOCUMENTS

| EP | 2682168 A1 | 1/2014 |
|---|---|---|
| GB | 1027551 A | 4/1966 |

(Continued)

OTHER PUBLICATIONS

Van der Meer et al., Diatomaceous Earth Filtration, BioProcess International, Sep. 2014, 12(8)s, pp. 25-28 (Year: 2014).*

(Continued)

*Primary Examiner* — Holly Kipouros
(74) *Attorney, Agent, or Firm* — Dickinson Wright PLLC

(57) ABSTRACT

A method and a kit for cell culture clarification, as well as a system or apparatus for clarifying a cell culture and purifying biomolecules of interest, are described. The cell culture comprises at least one biomolecule of interest. The method comprises adding one or more compounds to the cell culture that allow the formation of floccules of solutes and/or particulates in said cell culture harvest, adding an amount of diatomaceous earth (DE) to said cell culture harvest, agitating the obtained solution, and transferring said solution to a filtration vessel comprising a support filter having a surface, whereby the diatomaceous earth in said solution forms a layer on said surface and filtering said harvest solution through said layer and support filter.

12 Claims, 4 Drawing Sheets

(51) Int. Cl.
  *C12M 1/12* (2006.01)
  *C12M 1/34* (2006.01)
(52) U.S. Cl.
  CPC .............. *B01J 20/14* (2013.01); *C07K 16/00* (2013.01); *C12M 23/06* (2013.01); *C12M 25/02* (2013.01); *C12M 27/02* (2013.01); *C12M 41/40* (2013.01)

(56) References Cited

U.S. PATENT DOCUMENTS

| | | | |
|---|---|---|---|
| 2001/0043916 | A1 | 11/2001 | McNeilly et al. |
| 2006/0051845 | A1 | 3/2006 | Kikuchi et al. |
| 2013/0012689 | A1 | 1/2013 | Singh et al. |
| 2013/0225846 | A1* | 8/2013 | Domaille .................. C11B 1/02 554/206 |
| 2013/0309757 | A1 | 11/2013 | Kim |
| 2015/0004646 | A1 | 1/2015 | McNerney et al. |
| 2015/0147811 | A1* | 5/2015 | Thomas .................. C12N 1/02 435/308.1 |
| 2015/0252317 | A1 | 9/2015 | Lipkens et al. |
| 2018/0051275 | A1* | 2/2018 | Carter .................. C12N 7/00 |
| 2019/0315800 | A1* | 10/2019 | Gagnon .................. C07K 1/34 |

FOREIGN PATENT DOCUMENTS

| | | |
|---|---|---|
| GB | 1436323 A | 5/1976 |
| JP | S5626193 A | 3/1981 |
| WO | 2005073252 A1 | 8/2005 |
| WO | 2014123485 A1 | 8/2014 |
| WO | 2015130222 A1 | 9/2015 |

OTHER PUBLICATIONS

Tang et al., Use of colloid chitin and diatomaceous earth in continuous cake-filtration fermentation to produce creatinase, 1998, Process Biochemistry, vol. 33, No. 5, pp. 519-526 (Year: 1998).*

O'Mahony et al., Capture of Bacteria from Fermentation Broth by Body Feed Filtration: A Solved Problem?, 2006, Biotechnol. Prog., 22, 471-483 (Year: 2006).*

Tjebbe Van Der Meer et al: "Diatomaceous Earth Filtration Innovative Single-Use Concepts for Clarification of High-Density Mammalian Cell Cultures Body Feed Filtration Successful for Plasma Fractionation", Bioprocess International, Sep. 1, 2014 (Sep. 1, 2014), pp. 25-28, XP055405806.

Georgina Espuny Garcia Del Real: "Scale-Down Characterisation of Post-Centrifuge Flocculation Processes and the Study of its Impact upon Downstream Processing during Mammalian Cell Antibody Production," Thesis submitted to University College London, Dec. 1, 2016, pp. 1-325.

Nripen Singh et al: "Clarification technologies for monoclonal antibody manufacturing processes: Current state and future perspectives," Biotechnology and Engineering, vol. 113, No. 4, Apr. 1, 2016, pp. 698-716.

Benjamin Minow et al: "High-Cell-Density Clarification by Single-Use Diatomaceous Earth Filtration," BioProcess Internationals 12(4), Apr. 1, 2014, pp. 2-9.

Sladjana Tomic et a: "Complete clarification solution for processing high density cell culture harvests", Separation and Purification Technology vol. 114, 2015, pp. 269-274.

Thurne: "Filtrox:Single-Use Clarification of Fermentation Broths"—"Microfiltration of high-value liquids by means of depth filter systems", XP-002782412, www.thurne.se/2016/11/17/filtrox-single-use-clarification-of-fermentation-broths/, Nov. 17, 2016. pp. 1-4.

Filtrox: Filtrodisc Bio Sd Single clarification in a new dimension—Disposable high performance microfiltration system—Easy scalable from lab to process, BNSDOCID: <XP_554871731_1>, date unknown, pp. 1-4.

Filtrodisc (TM) Bio SD., "Single Use Clarification in a New Dimension. Disposable High Performance Microfiltration System Easy Scalable from Lab to Process", Dec. 12, 2016, pp. 1-4 See figure 1, p. 1.

Tomic et al., "Complete clarification solution for processing high density cell culture harvests", 2014, Separation and Purification Technology, vol. 141, pp. 269-275.

* cited by examiner

CELL CULTURE CLARIFICATION

TECHNICAL FIELD

This disclosure concerns a method and a kit for cell culture harvest clarification as well as a system for clarifying a cell culture and purifying biomolecules of interest.

BACKGROUND

Purification of biomolecules, such as proteins including antibodies, antibody fragments, fusion proteins, enzymes and other recombinant proteins, typically begins with a clarification step in which cells and debris are removed so that the remaining supernatant or filtrate can be processed by methods that would otherwise be hampered by their presence. Their removal commonly involves physical methods such as centrifugation and filtration. This step sometimes involves the use of filtration materials with anion exchange capabilities, or the addition of anion exchange particles or soluble polymers directly to the biomolecule-containing harvest.

WO 2005/073252 describes a process for inactivating and removal of viruses from a fraction of human plasma comprising immunoglobulins, referred to as a crude immunoglobulin solution. To this purpose, the crude immunoglobulin solution is treated with caprylic acid with the purpose of inactivating viruses present in the sample. In a next step, the viral particles are removed in a last step by nanofiltration.

WO 2015/130222 discloses methods of purifying a target protein comprising contacting a cell culture harvest with at least one fatty acid having 7 to 10 carbon atoms, and allantoin in a supersaturating concentration to form a mixture, and separating solid materials to provide a solution comprising the target protein with a reduced load of contaminants. Addition of the fatty acid and allantoin precipitates the contaminants and/or the cell debris comprised in the cell culture harvest. The precipitates are eliminated by gravimetric sedimentation and/or centrifugation. The supernatant is afterwards filtered using a filtration means such as a depth filter.

WO 2014/123485 describes a method for protein purification from a cell culture harvest. This method comprises the steps of treating the cell culture harvest with caprylic acid and organic multivalent ions in the presence of a supersaturating amount of allantoin, and of contacting the solution with a non-ionic organic polymer (e.g. PEG). Finally, clarification is obtained by passing the solution through a depth filter.

The methods disclosed in the prior art present several drawbacks. Overall, the prior art methods result in a considerable loss of product yield and lack of reproducibility between different batches. Said methods also lack robustness, in particular when scaled-up. WO 2015/130222 and WO 2014/123485 present a high risk that precipitates or floccules are sucked into and block the depth filter or other filter used for clarification. These drawbacks become more challenging if associated with potential scale-ups and technology transfers of the processes implementing this technology. Additionally, the methods of the prior art comprise a significant number of steps thereby increasing the contamination and/or human errors risk.

It is the aim to provide a method and kit for cell culture clarification which overcome at least part of the above mentioned drawbacks.

SUMMARY OF THE DISCLOSURE

In a first aspect, a method for cell culture clarification comprises:

(a) adding one or more compounds to a cell culture harvest comprising biomolecules of interest, said one or more compounds facilitating the formation of floccules of solutes and/or particulates in said cell culture harvest,
(b) adding an amount of diatomaceous earth (DE) to said cell culture harvest;
(c) agitating the cell culture harvest to form a harvest solution,
(d) permitting said DE in said cell culture harvest solution to form a layer on a support filter having a surface; and
(e) filtering said harvest solution through said layer and support filter.

In a second aspect, a system for clarifying a cell culture and purifying biomolecules of interest is provided. More in particular the system comprises:

a vessel for receiving or producing a cell culture harvest,
a support filter with a surface, wherein said surface is impermeable to diatomaceous earth (DE) and, as such, allows formation of a layer of DE on said surface, wherein said support filter is present in said first vessel for receiving or producing a cell culture harvest or in a filtration vessel fluidly connected to said first vessel
a fluid driving mechanism for transferring said cell culture harvest to said filtration vessel and/or through said layer.

An alternate embodiment, an apparatus is described comprising a body with an inlet for receiving cell culture media, cells, clarification compounds including DE and an outlet; said outlet including a support filter comprising a surface designed to support the formation of a DE cake which filters out clarification compounds from the cell culture and an agitator for mixing said cell culture.

In a third aspect, a kit to facilitate the practice of any of the embodiments of the method is described. More in particular a kit is provided to facilitate the practice of the disclosed method, comprising one or more compounds chosen from the group of fatty acids having 7 to 10 carbon atoms and derivatives thereof, ureides and electropositive compounds; an amount of diatomaceous earth and a leaflet comprising instructions to a user.

The method, the system and/or the kit present several advantages. An increase of the cell culture flowrate during clarification by filtration and an increase of the throughput of the filter may be achieved. The number of operation steps is reduced, as the filtration cake formed by the diatomaceous earth does not require pre-flushing with water or equilibration with a buffer. Furthermore, the filtration cake can be flushed with chasing solution—in contrast with methods wherein a precipitate is allowed to form by settling—thereby improving the recovery step. Additionally, the method comprises a minimal number of steps to achieve the clarification of the cell culture. Specifically, polishing steps and associated buffer conditioning steps can be eliminated. This considerably reduces the processing time, complexity, work load, the contamination risk and the cost of the target biomolecule purification process.

DETAILED DESCRIPTION OF THE DISCLOSURE

Figure 1A:
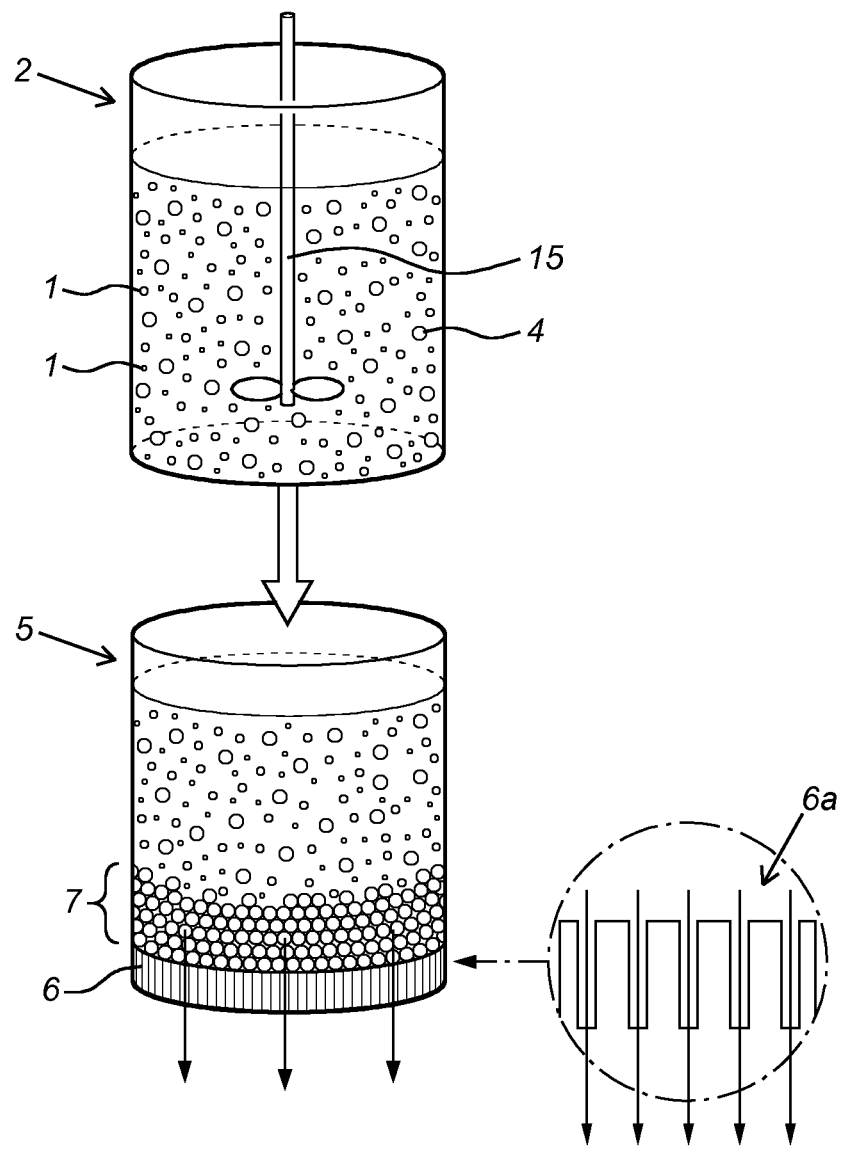
FIGS. 1A to 1C show schematic overviews of possible embodiments of disclosure systems for cell culture clarification.

First described is a method, a kit for cell culture clarification and a system for clarifying a cell culture harvest and purifying biomolecules of interest. The cell culture comprises at least one biomolecule of interest. "Biomolecules" includes proteins such as antibodies, antibody fragments, fusion proteins, enzymes, recombinant proteins, peptides, polypeptides or other biomolecules expressed by the cells.

Unless otherwise defined, all terms used in this disclosure, including technical and scientific terms, have the meaning as commonly understood by one of ordinary skill in the art to which this disclosure belongs. By means of further guidance, term definitions are included to better appreciate the teaching of the present disclosure.

As used herein, the following terms have the following meanings:

"A", "an", and "the" as used herein refers to both singular and plural unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed disclosure. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows, e.g. component, and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation. The expression "1% w/w" refers to what can be understood as 1g of respective component per 100 g of the formulation, the expression "1% w/v" refers to what could be understood as 1g of respective component per 100 mL of the formulation, the expression "1% v/v" refers to what can be understood as 1 mL of respective component per 100 mL of formulation.

The term "particulates" refers to solid particles suspended in a liquid.

The term "flocculation" refers to the aggregation, precipitation and/or agglomeration of insoluble particles caused by the addition of a suitable flocculating agent to a suspension. By increasing the particle size of the insoluble components present in the suspension, the efficiency of solid/liquid separations, such as by filtration or centrifugation, is improved. Flocculation of a cell culture leads to the formation of "floccules" which comprise host cell impurities such as cell material including cells and cell debris or host cell proteins, DNA or other components present therein.

The terms "Cell culture harvest", "culture harvest" and "harvest" are used herein as synonyms and refer to the unclarified cell culture obtained at the end of culturing cells in a bioreactor. The cultured cells or the grown cells also are referred to as host cells.

The term "bioreactor" as used herein refers to any device or system that supports a biologically active environment, for example for cultivation of cells or organisms for production of a biological product. This would include cell stacks, roller bottles, shakes, flasks, stirred tank suspension bioreactors, high cell density fixed bed perfusion bioreactors, etc.

The terms "molecule of interest" or "biomolecule of interest" or "target biomolecule" or "target molecule of interest" or "target biomolecule of interest" or "biomolecule" are used herein as synonyms and refer to an organic molecule in a living organism, having characteristics typical of molecules found in or secreted by living organisms including individual cells and that may be naturally occurring or may be artificial (not found in nature and not identical to a molecule found in nature). Example target biomolecules include but are not limited to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides.

The terms "diatomaceous earth structure", "diatomaceous earth filter cake", "diatomaceous earth filtration cake" and "diatomaceous earth cake" are used herein as synonyms and refer to the structure formed by the diatomaceous earth during the filtration process. The diatomaceous earth used in the method or system according to the disclosure can be of various "grades", wherein the grade gives an indication of the size of the pores present in the diatomaceous earth. The grade of diatomaceous earth used in a method or system according to the disclosure depends on the morphology, particularly the size and the shape, of the cells from which a clarified cell culture is to be obtained. For example, for CHO cell cultures, Celpure 300® grade or Celpure 100® grade can be used. For CHO cell cultures grown in an adherent environment such as with a high cell density fixed bed bioreactor, Cellpure 100® grade or Celpure 65® grade can be used. The smaller the floccules, the finer the grade of DE needed, in general.

The term "filtration" or "separation" refers to the removal of the aqueous phase, containing the soluble biomolecules of interest, from the insoluble particles, for example following flocculation of the cell culture harvest.

As used herein, the term "free fatty acid" refers to an unmodified fatty acid, i.e. a fatty acid not converted into a salt, an amide, an ester etc. As used herein, the term "fatty acid derivative" refers to a salt of the free fatty acid or a fatty acid whose carboxylic acid group is reversibly converted into another group to form amides, esters, glycerides, sugars.

The term "ureide" refers to any class of organic compound derived from urea by replacing one or more of its hydrogen atoms by organic groups including compounds derived from the acylation of urea, and diureide compounds which contain two molecules of urea, or radicals thereof. Ureides can have a cyclic or acylclic structure and include but are not restricted to allantoin and allantoic acid.

The term "electropositive compound" is to be understood as molecules having a positive net charge and able to bind to or form complexes with negatively charged molecules.

The term "purification" as used herein refers to the substantial reduction of the concentration of one or more target impurities or contaminants relative to the concentration of the biomolecules of interest.

In a first aspect, a method for cell culture clarification comprises:
(a) adding one or more compounds to a cell culture harvest comprising biomolecules of interest, said one or more compounds facilitating the formation of floccules of solutes and/or particulates in said cell culture harvest,
(b) adding an amount of diatomaceous earth (DE) to said cell culture harvest;
(c) agitating the cell culture harvest to form a harvest solution,
(d) permitting said DE in said cell culture harvest solution to form a layer on a support filter having a surface; and
(e) filtering said harvest solution through said layer and support filter.

This method leads to fast and easy removal of host cell derived impurities including the cells themselves, cell debris, and other unwanted materials allowing efficient further processing of the cell culture which would otherwise be threatened by the host cell derived impurities. The disclosure thus provides a robust and high-throughput method for cell culture clarification. Concomitantly, the method of the disclosure reduces the number of post-clarification steps needed to obtain the molecule of interest, therefore reducing complexity of and time for DSP processing and increasing yield due to elimination of these additional post-clarification steps.

The formation of floccules in the cell culture is achieved in step (a) through addition of compounds that stimulate the precipitation of impurities and/or the aggregation or agglomeration of impurities, precipitates or particulates present in the cell culture. Specifically, precipitated fractions contain host cell impurities, e.g. host cells, host cell proteins and host cell DNA, thus significantly minimizing the content of host-cells impurities in the non-precipitated fraction of the first solution.

Flocculation of host cell impurities is achieved due to the ability of the added compounds to exert hydrophobic interactions, ionic interactions and/or hydrogen bonding with host cells related impurities present in the cell culture harvest or other mechanisms of interaction.

Addition of the compounds changes the physical properties of the suspension comprising the host cells, cell debris, the compounds added and/or the various impurities and the target biomolecules. Indeed, the average particulate size in the cell culture harvest increases.

Addition of an amount of DE to the cell culture harvest, suspension or solution implements a filtering mechanism of the treated/flocculated harvests without altering the ability of the added compounds to remove host-cell related impurities. In an embodiment, the amount of DE may be based on the amount of solids in the harvest, including by calculation of wet cell weight as further described below. In an embodiment, DE is added after addition of the compounds, such as 30 to 45 min after. In another embodiment, an amount of DE is added prior to addition of the compounds. In an alternate embodiment, an amount up to 100% of the DE is added simultaneously with the compounds.

Agitation of the cell culture harvest may be continuous or discontinuous. It can be maintained for 5 to 60 min, for 8 to 40 min, for 10 to 30 min, for 15 to 20 min. Agitation is maintained at any frequency that is sufficient to keep the solution mixed homogeneously, preferably agitation frequency is 60 to 240 rpm. Agitation can be achieved by several means known in the art such as mixing of the solution by a mixer present in the vessel, or by shaking or rocking the vessel.

Afterwards, the solution is filtered, thereby removing floccules and resulting in a clarified cell culture. To achieve such filtering, a support filter having a surface may be present in the bioreactor, wherein the support filter has a surface which is impermeable to diatomaceous earth. In an alternate embodiment, permitting step d) comprises the step of transferring said agitated harvest solution to a filtration vessel comprising a support filter having a surface and allowing to form DE layer on said surface. Optionally, a pressure differential is allowed to form the DE layer on the surface. In order to allow the formation of the DE layer, the agitation will be ceased or temporarily paused, especially in the design where the support filter is integrated in the first vessel. Cessation of agitation is not needed when the addition of compounds and DE occurs in a vessel separate from the vessel comprising the surface. In this case, constant agitation is desired in order to ensure homogeneity of the solution.

The DE cumulates on one side of the surface and gradually builds-up into a structure referred to as a "DE cake" (or "DE layer") structure comprising a plurality of channels or paths. After a period of time, the formed DE cake structure serves as a filtration media (i.e. a filter). The large matter such as cells, cell debris, and other large non-target compounds of the solution obtained) are retained by the DE cake structure, whereas the target biomolecules, having a smaller size, flow through the channels of the DE cake structure. To facilitate such flow, a pump or other pressure dispense aid or other fluid driving mechanism is used as further described in embodiments below. A clarified cell culture comprising the biomolecules of interest is thereby obtained.

The size or the diameter of the channels formed by the DE cake structure is defined by the particle size of the DE added to the first solution. The DE particle size may be chosen according to the properties of the cell culture and/or the properties of the cells used to express the molecule of interest (this includes the type of cells (e.g. CHO cells) and the cell density of the harvest to be clarified). The DE can be of various grades that are commercially available on the market. For example, for CHO cell cultures, Celpure 300® grade or Celpure 1000® grade can be used in traditional suspension bioreactors. Finer grades of DE must be used for high cell density bioreactors with a fixed bed on which cells adhere.

The use of diatomaceous earth to facilitate filtration overcomes the limitations imposed by the physical changes of the cell culture after flocculation which tend to render routine clarification complex. For instance, in case of depth filtration, a very significant surface of depth filters is needed to clarify the first solution comprising the formed precipitates. To avoid having low throughput, the precipitates of the flocculated solution are allowed to settle under gravity followed by a transfer of the obtained supernatant into the depth filter as described in WO 2015/130222. This approach lacks robustness, requires significant customization of manifolds and presents a high risk that precipitates or floccules are sucked into the system and block the depth filter. Using the clarification method of WO 2015/130222, the precipitated fraction still contains some valuable target material that is not recovered by further depth filtration.

Furthermore, said method requires additional operations to achieve the desired quality of clarified cell culture harvest, i.e. hold period to allow the particulate matter or floccules to settle.

Addition of DE to the solution does not alter the performance of the precipitation compounds of step (a) or the reduction of the cell impurities. At the same time, allowing the precipitants to settle under gravity is no longer required. The obtained solution is preferably constantly under agitation. The DE cake structure is formed on the surface and serves as a filter as described above. This allows achieving significant operational advantages including shorter processing time, less process steps, less process materials, less equipment and solutions, without compromising the quality of the clarified harvest.

The method, in particular, the use of DE allows to:
- increase the flowrate during filtration: flowrate of 1000-2000 LMH (liters per square meter per hour) using diatomaceous earth versus 100 to 150 LMH in filtration using methods in which cell impurities or debris are precipitated (such as when using depth filters available commercially),
- increase the throughput of the filter: the DE cake structure allows to process at least 400 L of cell culture comprising precipitate per 1 $m^2$ of filter cake, whereas the state of the art filters are able to process at most 300-350 $L/m^2$ of cell culture comprising precipitate formed as per the procedure described above,
- achieve the turbidity value for filtrate pool below 5 NTU and therefore eliminate necessity of any further depth filtration in the process. Filtrate can be introduced directly on sterilizing-grade filter and further processed,
- reduce the method steps required for achieving the clarification of the cell culture. For example, sub-steps of flushing with water and equilibrating with isotonic buffer are not required for a filter cake formed from DE according to the present disclosure, however it is the case for the methods of the prior art that implement standard commercially available depth filters. This leads to a considerable cost and time reduction required to achieve desirable quality of clarified cell culture harvest.

In a further embodiment, the compounds allowing the formation of floccules are chosen from the group of fatty acids having 7 to 10 carbon atoms and derivatives thereof, ureides and electropositive compounds. The different compounds of step (a) might be mixed prior to their addition to the cell culture. The compounds of step (a) might also be added separately to the cell culture. In this case, the compounds can be introduced in any order or sequence. In further embodiment, step (a) and (b) are implemented simultaneously. This is advantageous as it reduces the number of steps necessary for obtaining a clarified cell culture.

The inventors have found that compounds from the above-mentioned group are especially well suited to induce precipitation and flocculation of host cell culture associated impurities in step (a) of the method according to the disclosure. Fatty acids having 7 to 10 carbon atoms are thought to exert hydrophobic interactions with hydrophobic host cell derived impurities, causing their agglomeration. Derivatives of fatty acids having 7 to 10 carbon atoms are equally well suited as unmodified fatty acids in step (a) of the disclosure. These derivatives include but are not limited to fatty acid salts, including sodium salts and potassium salts of the respective free fatty acids.

Ureides are organic compounds derived from urea by replacing one or more of its hydrogen atoms by organic groups including compounds derived from the acylation of urea, and diureide compounds which contain two molecules of urea, or radicals thereof. Ureides can have a cyclic or acylclic structure and include but are not restricted to allantoin and allantoic acid. Ureides were found to be particularly well-suited as binding agents in step (a) of the method of the current disclosure. Without wishing to be bound by theory, ureides are thought to function as binding agents by interacting with impurities in solution, for example through hydrogen bonding.

Electropositive compounds are well suited for use as flocculating agents in step (a) of a method according to one embodiment. Electropositive compounds are thought to bind negatively charged components derived from host cells such as, but not limited to, nucleic acids including host cell DNA and RNA.

The inventors have found that compounds selected from one of the three abovementioned classes of compounds, when applied as flocculating agents in step (a) of a method according to the current disclosure, result in exceptional clearance of cell cultures comprising a biomolecule of interest.

Preferably, in step (a) one or more fatty acids having 7 to 10 carbon atoms or derivatives thereof, allantoin and one or more electropositive compounds are added. This combination was found by the inventors to excel when applied in step (a) of the disclosed method.

In a further embodiment of the method for cell culture clarification, the cells comprising at least one biomolecule of interest or target biomolecule are grown in at least one bioreactor; the wet cell weight of the cell culture is determined, a composition comprising at least one fatty acid having 7 to 10 carbon atoms, allantoin and at least one electropositive compound are added to the cell culture; diatomaceous earth is added and the obtained solution is filtered in at least one filtration vessel.

In an embodiment, the compounds added in step (a) are incubated with the cell culture harvest for 5 to 360 minutes, preferably 15 to 240 minutes, more preferably 60 to 120 minutes, most preferably 30 to 60 minutes, or for an intermediate interval. In an embodiment, after addition of the compounds, the cell culture harvest is subject to continuous agitation at 60 to 120 rpm. Said cell culture is preferably maintained at room temperature. The incubation period allows the flocculation to take place while continuous agitation prevents the deposition of the compounds or the solutes/particulates suspended in the cell culture therefore allowing optimal contact between host cell derived impurities and the compounds added to the cell culture in step (a).

The unclarified cell culture harvest comprising at least one biomolecule of interest can be obtained by growing cells in at least one bioreactor. The bioreactor can be any type of bioreactor known to the person skilled in the art such as stirring tank bioreactor, perfusion bioreactor, wave bioreactor, cylindrical bioreactor, bag bioreactor, moving bed bioreactor, packed bed bioreactor, fibrous bioreactor, membrane bioreactor, batch bioreactor, high cell density perfusion bioreactor with fixed bed or continuous bioreactor. The bioreactor can be of any shape and can be made from any material, for example, stainless steel, glass, or plastic. Where the bioreactor in which the cell culture production occurs is a high-density bioreactor with a fixed bed, the compounds of step (a) and DE of step (b) are added to a separate intermediate vessel as the DE cannot penetrate the fixed bed volume and properly form a DE cake. However, in a traditional suspension bioreactor, the two steps can occur in the bioreactor itself. Accordingly, in a further embodiment, the cell culture resides in a bioreactor in which cell culture production occurs and the compounds of step (a) are added directly to said bioreactor. The addition is performed after reaching a desired stage of cell culture such as a predetermined cell density or after a predetermined cell culture time, thereby obtaining a cell culture harvest. This is advantageous as it considerably reduces work load and does not require any intermediate tanks, lines or set-ups.

In an embodiment, the cells are grown in the presence of adapted culture medium in the bioreactor. Adapted culture medium refers to the composition of the medium which is required for the growth of the cells. Said compositions are known to the person skilled in the art and generally comprise salts, vitamins, amino acids, sugars or any combination thereof. The culture medium can be preheated at temperature of from 20 to 40° C., preferably from 25 to 38° C., more preferably from 30 to 37° C. In a further embodiment, said culture medium is pre-heated at about 37° C.

In an embodiment, the diatomaceous earth is added directly into the bioreactor. This is advantageous as it considerably reduces work load and does not require any intermediate tanks, lines or set-ups.

Alternatively, the cell culture harvest comprising at least one biomolecule of interest can be removed from the bioreactor prior to step (a). Accordingly, in another further embodiment, the cell culture resides in an intermediate vessel downstream of a bioreactor producing said cell culture and the compounds of step (a) are added to said intermediate vessel. The inventors have found that use of an intermediate vessel for performing step (a) of the method can be advantageous when the formation of floccules could for example damage the bioreactor or when adequate agitation of the cell culture with the added compounds is not possible in the bioreactor wherein the cell culture production occurred.

In one embodiment, the compounds of step (a) comprise 0.1% to 1.0% v/v fatty acid. In a further embodiment, the compounds of step (a) comprise 0.6% to 3% w/v allantoin, depending on the type of cell culture used, but must reach supersaturation level to optimally perform. In another further embodiment, the compounds of step (a) comprise 0.01% to 1% w/v electropositive compound. The inventors have found that when these compounds are included in step (a) in the amounts as described, they allow effective formation of floccules in the cell culture. More preferably the compounds of step (a) comprise 0.3% to 0.6% w/v fatty acid, 1.0% to 2.0% w/v allantoin and/or 0.05% to 0.1% w/v electropositive compound. Most preferably the compounds of step (a) comprise 0.4% to 0.5% v/v fatty acid, 1.2% to 1.8% w/v allantoin and/or 0.06% to 0.08% w/v electropositive compound. The compounds can be in liquid or solid form (such as a mixture of powders).

In an embodiment, the cell culture wet cell weight (WCW) is determined and the amount of DE added is from 20 to 60% of said cell culture wet cell weight (WCW), preferably from 25 to 55%, more preferably from 30 to 50%, even more preferably from 35 to 45% most preferably about 40% of the cell culture WCW. The WCW is determined per any method known to the person skilled in the art. For certain bioreactors, optimization of DE amount and grade is necessarily empirical. When the amount of DE exceeds 60% of the WCW, no further improvement in capturing and filtering of host cell impurities by the DE cake structure during filtration is seen, whereas the cost due to higher amount of DE increases, as well as the filtration time due to the increased thickness of the DE cake. Thus when an amount of DE exceeding 60% of the WCW is used, the efficiency of the cell culture clarification process may be reduced.

Preferably, the WCW is determined as follows: cell culture samples are withdrawn from the bioreactor after reaching the desired stage of cell culture and at least 3 samples are collected.

The volume of each sample may vary from 15 ml to 50 ml or any other representative volume depending on the bioreactor's scale. The samples are centrifuged at 4000 to 5000 g for 5 to 10 minutes to sediment cells. The obtained supernatant is discarded and WCW is calculated based on the difference between the weight of empty centrifugal tubes and the weight of the centrifugal tubes containing settled-down cells. The average of the three measurements is calculated and recorded as WCW in gram per liter.

The general structural formula of free fatty acids is $CH_3(CH_2)_nCOOH$, wherein n is an integer from 4 to 12 inclusive, preferably from 5 to 8 inclusive. The fatty acid may be enanthic acid (heptanoic acid), caprylic acid (octanoic acid), pelargonic acid (nonanoic acid), capric acid (decanoic acid) or any combination thereof. The fatty acid may be added in the form of a fatty acid derivative for example a fatty acid salt, such as a sodium salt, for example sodium caprylate. The fatty portion of the fatty acid or fatty acid derivative may consist of a linear "straight" chain of carbon atoms. In some embodiments, the fatty portion of the fatty acid or fatty acid derivative may consist of a branched chain, such as 2-ethylhexanoic acid, which contains a 2-carbon chain at the number 2 position of the primary 6-carbon chain, producing a total of 8 carbon atoms. The fatty acid or fatty acid derivative may include a double bond at any position in the carbon chain. The fatty acid or fatty acid derivative carbon chain may contain 6 or 7 or 8 or 9 carbon atoms. The free fatty acid might also be nonenoic acid with a terminal double bond.

In one embodiment, the electropositive compound is any electropositive charged particle such as electropositive polysaccharide, electropositive polymer, chitosan, chitosan derivatives, synthetic polymers such as polydiallyl dimethylammonium chloride (pDADMAC or polyDDA), benzylated poly(allylamine) and polyethylenimine, commercially available particles like TREN (BioWorks, WorkBeads TREN, high) or cationic surfactants like hexadecyltrimethylammonium bromide (also known as CTAB) or any combination thereof. Without wishing to be bound by theory, electropositive polymers are thought to act as flocculation agents because they can simultaneously bind several negatively charged contaminants such as host cell DNA and RNA causing formation of a floc. The abovementioned electropositive compounds were found to perform extremely well (floc formation and floc size) when combined with filtration using DE according to the method of the disclosure.

In an embodiment, the electropositive compound may be deacetylated chitin (chitosan, also referred to poly(D-glucosamine)) with a deacetylation degree of at least 75% and a molecular weight of from 30 kDa to 1000 kDa, preferably from 300 kDa to 400 kDa, more preferably from 325 kDa to 375 kDa or any intermediate value. Chitosan is well suited for flocculation of mammalian cell cultures as it is produced from non-mammalian sources (typically arthropod shells) and is also available in a highly purified form that is low in heavy metals, volatile organics and microbial materials. The deacetylation imparts limited solubility on insoluble chitin and the amino groups on the polymer result in a polycationic material at acidic and neutral pH that can interact with polyanions, such as DNA and cell culture debris (typically negatively charged). Optionally, the composition further comprises other electropositive compounds in addition to chitosan or instead of chitosan.

In an embodiment, after addition of the compounds in step (a), the pH of the solution is adjusted such that it is comprised between 4 and 7, preferably between 5.0 and 6.0, more preferably between 5.1 and 5.4, most preferably between 5.25 to 5.35, or an intermediate value. Adjusting the pH improves the clearance of host cell impurities present in the cell culture, such as host cell proteins and host cell DNA, during the clarification step. Furthermore, acidic pH changes the average size distribution of particles contained in the non-clarified cell culture harvest thereby improving the performance of step (c). Another important advantage of pH adjustment after addition of the compounds of step (a) is to ensure consistency and reproducibility of the clarification from batch to batch operation, during scale-ups and transfers. Adjustment of conductivity can also impact target protein recovery so it is also preferable to engage in similar optimization activity for this characteristic.

In a second aspect, a system for clarifying a cell culture and purifying biomolecules of interest comprises:
- a first vessel for receiving or producing a cell culture harvest,
- a filtration vessel fluidly connected to said vessel and having a support filter with a surface, wherein said surface is impermeable to diatomaceous earth (DE) and, as such, allows formation of a layer of DE on said surface,
- a fluid driving mechanism for transferring said cell culture harvest to said filtration vessel and/or through said layer.

The term impermeable above is used to mean that the surface is impermeable to the vast majority (nearly 100%) of DE particles. The term "fluid driving mechanism" is to be understood as a mechanical device using suction or pressure to raise or move fluids (including liquids or gases). An example of such mechanism is a pump.

The vessel is fluidly connected to a filtration vessel. Each of the vessel and the filtration vessel comprises at least one inlet and one outlet. Preferably, the outlet of the vessel is fluidly connectable to the inlet of the filtration vessel. The cell culture can be introduced into or passed through the filtration vessel using at least one fluid driving mechanism such as a pump. Preferably, the flow rate and/or the pressure at the inlet of the filtration vessel is measured using adapted measurement means provided in said inlet. The filtration vessel and/or the measurement means can be any means known by the person skilled in the art. For example, the filtration vessel can be a housing made of polymer material that is assembled around a surface which is impermeable for diatomaceous earth particles. Said housing and polymer material membrane defines a filtration surface area of at least 20 to 30 $cm^2$ for each 1 L of flocculated cell culture harvest.

The filtration vessel can be of any shape. It is preferably cylindrical having a diameter of about 5.5 cm and a height of about 4.5 cm which is sufficient to process up to 1 L of cell culture harvest. Preferably, the filtration vessel comprises an inlet and an outlet, each having at least one port for connecting said inlet and/or outlet to other lines or vessels and at least one vent port to remove air during the filling of the filtration vessel. An inlet and/or an outlet of the filtration vessel could be equipped with pressure sensors or other sensors or control elements if needed.

In an alternate embodiment, an apparatus is described comprising a body with an inlet for receiving cell culture media, cells, clarification compounds including DE and an outlet; said outlet including a support filter comprising a surface designed to support the formation of a DE cake which filters out clarification compounds from the cell culture and an agitator for mixing said cell culture. In this integrated design, the surface is present at the outlet of said first body, which may be a bioreactor as described above. In this integrated design, the surface is preferably present at the bottom of said first vessel where the drain or outlet would reside, but it could be positioned anywhere such that the direction of fluid flow would be through the surface and the DE layer. After completion of the cell culture process, the compounds and DE are added and the cell culture harvest is agitated in order to achieve a (homogeneous) solution. Agitation can occur via any means known in the art, such as via a mixer present in the vessel or by shaking or rocking said vessel. The DE cake is subsequently allowed to be formed on the surface of the support filter by pausing the agitation and allowing (e.g. by gravity) or facilitating (e.g. by pump) a pressure differential. In a final step, the solution is filtered through the formed DE cake and support filter and transferred to a downstream unit for further processing. The same pressure differential or another one moves the solution through the layer and support filter and out. Integration of the support filter in the bioreactor allows for an optimized design minimizing the required space needed for installation and functioning.

The use of DE as a cake filter further permits to reduction of the necessary surface area. For example, a maximum of 250 $cm^2$ for each 1 L of flocculated cell culture harvest will suffice to provide an effective cell culture clarification. Alternatively a maximum of 200 $cm^2$ can be used for each 1 L. Even more 150 $cm^2$, 100 $cm^2$ or 50 $cm^2$ may suffice for each 1 L of flocculated cell culture harvest.

The polymer material of the housing could be polyethylene terephthalate and the support filter can be made of polyethylene having a porosity depending on the grade of DE used which could range from 0.1 micrometers to 50 micrometers, or from 0.7 micrometers to 30 micrometers or from 7 to 12 micrometers. The support filter can be a simple porous or mesh membrane or support. However, in order to prevent flow of the flocculates through the surface of the support filter before the DE cake is formed thereon, the support filter can be an actual filter of appropriate characteristics based on the cell culture. Examples are a polyethylene membrane, a cellulose depth filter, or a polyethylene membrane.

After completion of the filtration step, the DE structure or DE cake can be flushed with proper chasing buffer to recover the biomolecule of interest retained in the filter cake and can then be discarded. Preferably, the chasing buffer is isotonic to the cell culture harvest in terms of pH and conductivity. A person skilled in the art can easily select a proper buffer isotonic to the cell culture harvest that is subject to clarification. For instance, a preferred chasing buffer used to chase harvest clarified at pH 5.3 has the following composition: 50 mM sodium acetate, 125 mM sodium chloride, pH 5.30. If the harvest is clarified in neutral conditions, then a preferred chasing buffer has the following composition: 20 mM sodium phosphate, 125 mM sodium chloride, pH 7.0. This is a distinction from clarification methods involving precipitation and settlement of non-target material and molecules and withdrawal of the obtained supernatant.

In another embodiment, a second filtration vessel is comprised in the system, downstream of the filtration vessel or body and upstream of the purification unit. The second filtration vessel may be similar to or different from the first filtration vessel. For example, optionally, a depth filter is positioned downstream filter vessel. The depth filter is chosen such that the target biomolecules pass though it while retaining as much as possible of other eventual contaminants. This further reduces the presence of contaminant in the clarified cell culture and further improves the clarity of the obtained filtrate should it be required for further application, such as purification with a purification unit. In certain embodiments, the filtration vessel is a microfiltration vessel to control bioburden.

The clarified cell culture might be further conditioned and/or processed to obtain purified biomolecules. A downstream purification unit for purifying biomolecules of interest from said cell culture may be used in the system. The pH and/or conductivity of the clarified cell culture might be adjusted for further treatments. The clarified cell culture harvest can be:

passed through an additional functionalized filter,
concentrated and buffer exchanged by ultrafiltration and diafiltration,
processed by high performance tangential flow filtration,
precipitated from the clarified cell culture by polyethylene glycol,
selectively precipitated from the clarified cell culture by a kosmotropic salt such as ammonium sulfate, sodium sulfate, potassium phosphate, sodium citrate, or potassium citrate,
processed by a chromatography such as affinity chromatography, cation exchange chromatography, anion exchange chromatography, steric exclusion chromatography, preferential exclusion chromatography, hydrophobic interaction chromatography, hydroxyapatite chromatography or so-called mixed mode chromatography, where a given chromatography medium comprises multiple chemical functionalities able to achieve different fractionation results than the constituent functionalities, applied sequentially, or any combination of the above-mentioned treatments.

In a third aspect, a kit facilitates the practice any of the embodiments of the method as described above for cell culture clarification comprising one or more compounds chosen from the group of fatty acids having 7 to 10 carbon atoms and derivatives thereof, ureides and electropositive compounds; diatomaceous earth and a leaflet comprising instructions to the user. In an embodiment, the kit comprises one or more fatty acids having 7 to 10 carbon atoms or derivatives thereof, allantoin and one or more electropositive compounds. The fatty acid is selected from the group comprising enanthic (heptanoic) acid, caprylic (octanoic) acid, pelargonic (nonanoic) acid, or capric (decanoic) acid or any combination thereof. In a further embodiment, the fatty acid and/or the allantoin and/or the electropositive compound and/or the diatomaceous earth are in solid form, more preferably in powder form.

In a further embodiment, the kit comprises a system as described above for clarifying a cell culture and purifying biomolecules of interest.

DETAILED DESCRIPTION OF FIGURES

Figure 1B:
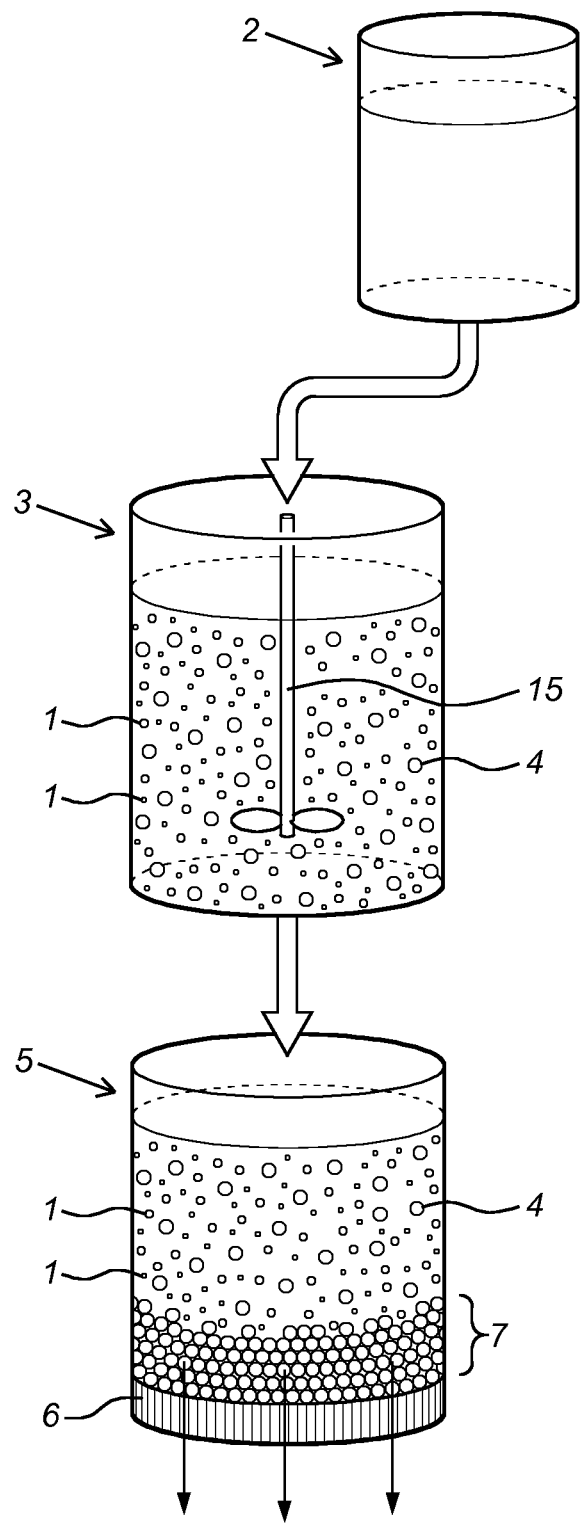
Figure 1C:
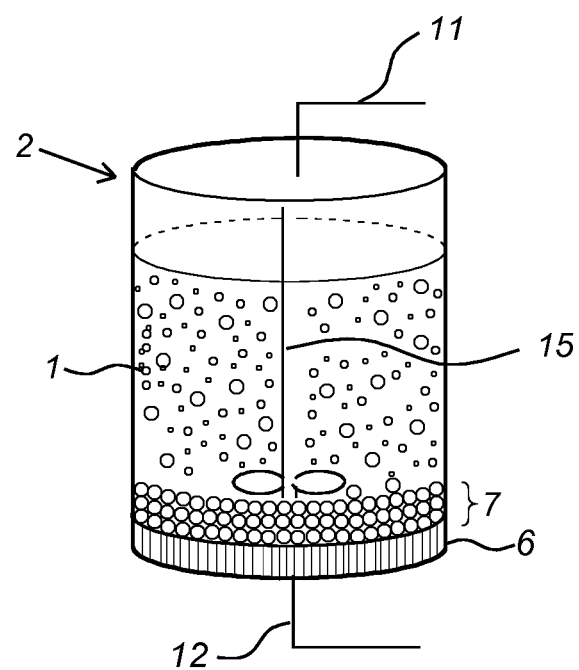

FIGS. 1A to 1C: Show Schematic Overviews of Possible Configurations for Performing Methods for Cell Culture Clarification According to Embodiments of the Disclosure.

According to an embodiment of the method for cell culture clarification, one or more compounds that alter the physical properties of the cell culture allow the formation of floccules (1) of solutes and/or precipitates are added to the cell culture. These compounds can be added, according to an embodiment of the disclosure, directly to the bioreactor (2) in which cell culture production occurs and wherein the cell culture comprising molecules of interest resides (setup as shown in FIG. 1A). According to an alternative embodiment, the cell culture is first transferred from the bioreactor (2) to an intermediate vessel (3) and the above mentioned compounds are added to the cell culture residing in that intermediate vessel (3) (setup as shown in FIG. 1B). This particular design could be advantageous in case of the bioreactor being a high cell density bioreactor with a fixed cell bed, which is less suitable to accommodate the addition of the compounds and/or DE. The use of an intermediate vessel (3) can be advantageous when the formation of floccules (1) could, for example, damage the bioreactor or impede the functioning thereof or when adequate agitation of the cell culture with the added flocculation compounds is not possible in the bioreactor wherein the cell culture production occurred. Diatomaceous earth (4) is added to the cell culture as well, either directly to the cell culture residing in the bioreactor (2) (setup as shown in FIG. 1A) or to the cell culture residing in the intermediate vessel (3) (setup as shown in FIG. 1B). In a next step which is identical for both embodiments, the solution containing floccules (1) of solutes and/or precipitates is transferred to a filtration vessel (5) comprising a support filter (6, close up in FIG. 1A) which is impermeable to diatomaceous earth (4). FIG. 1A and 1B show the formation of a layer or cake (7) of diatomaceous earth (4) on the surface (6a), thereby filtering the solution through the cake (7) and the support filter (6). Arrows illustrate the flow of clarified cell culture through the surface (6a) in FIGS. 1A and 1B. The location of the surface is dictated by the differential pressure direction for fluid transmission. The filtration vessel 5 can be a rigid vessel or a single use bag with support, either with or without a mixer known in the art for agitation.

In an alternate embodiment, shown in FIG. 1C an integrated system is provided wherein a support filter is present in a bioreactor (2), preferably at the bottom of the bioreactor near or at an outlet (12). In this set-up, the cell culture is grown in the bioreactor. In a subsequent step, compounds and DE are added—either sequential or simultaneous—directly into the bioreactor while being agitated (either via mixing, or rocking) after which the DE layer (7) is formed on the surface (6a) present in the bioreactor and which allows filtering through the filter (6) and the layer (7). The filtered output may subsequently be transferred to a (micro) filter and purification unit, e.g. a chromatography column. To this purpose, the bioreactor may be in fluid connection with such a (micro)filter or purification unit. In an embodiment, an intermediate vessel (not shown) may be positioned between the bioreactor and the downstream filter or purification unit, for temporarily collecting the clarified harvest coming from the bioreactor. A fluid driving mechanism such as a pump may ensure the transferring of the clarified harvest from one unit to another.

Figure 2A:
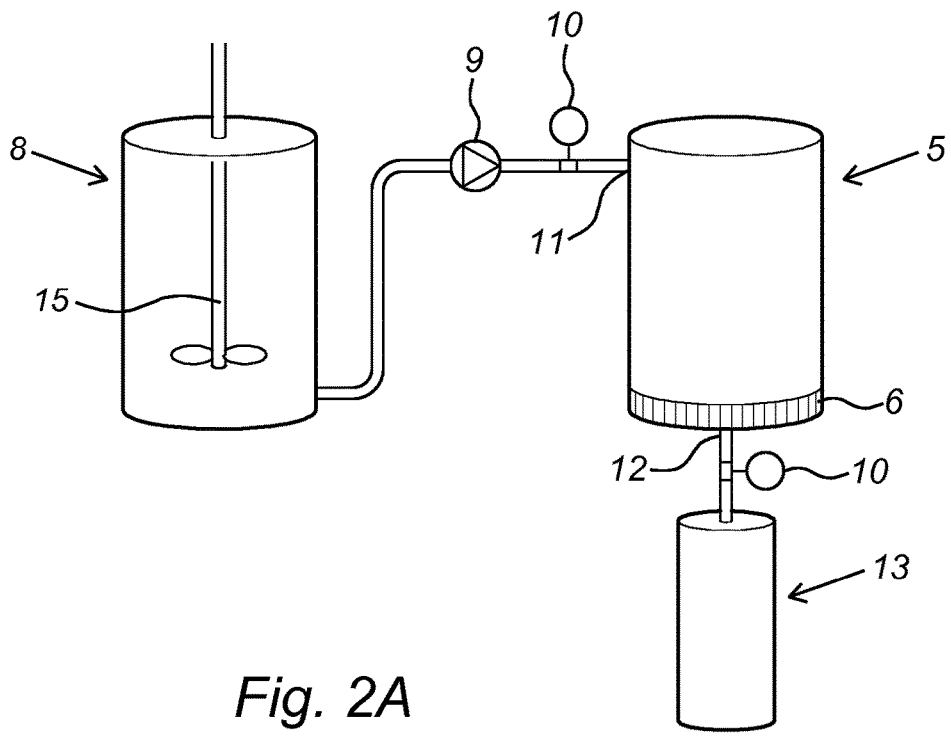
FIGS. 2A and 2B show schematic overviews of illustrative systems for clarifying a cell culture and purifying biomolecules of interest according to embodiments of the current disclosure.

FIG. 2A Shows a Schematic Overview of a System for Clarifying a Cell Culture and Purifying Biomolecules of Interest, According to an Embodiment of the Disclosure.

The system for clarifying a cell culture and purifying biomolecules of interest depicted in FIG. 2A consists of a vessel (8) for receiving, producing or temporarily storing a cell culture, such as a bioreactor or an intermediate vessel, optionally provided with a mixer (15) which is fluidly connected to a filtration vessel (5). The surface (6a) present in the filtration vessel (5) is impermeable to diatomaceous earth thereby allowing formation of a layer or cake of diatomaceous earth on the surface (6a). The system further comprises a pump (9) for transferring the cell culture from the vessel (8) to the filtration vessel (5) and pressure sensors (10) located at the inlet (11) and outlet (12) of the filtration vessel (5). Finally, a purification unit (13) which is located downstream of the filtration vessel (5) allows the purification of biomolecules of interest from the cell culture.

Figure 2B:
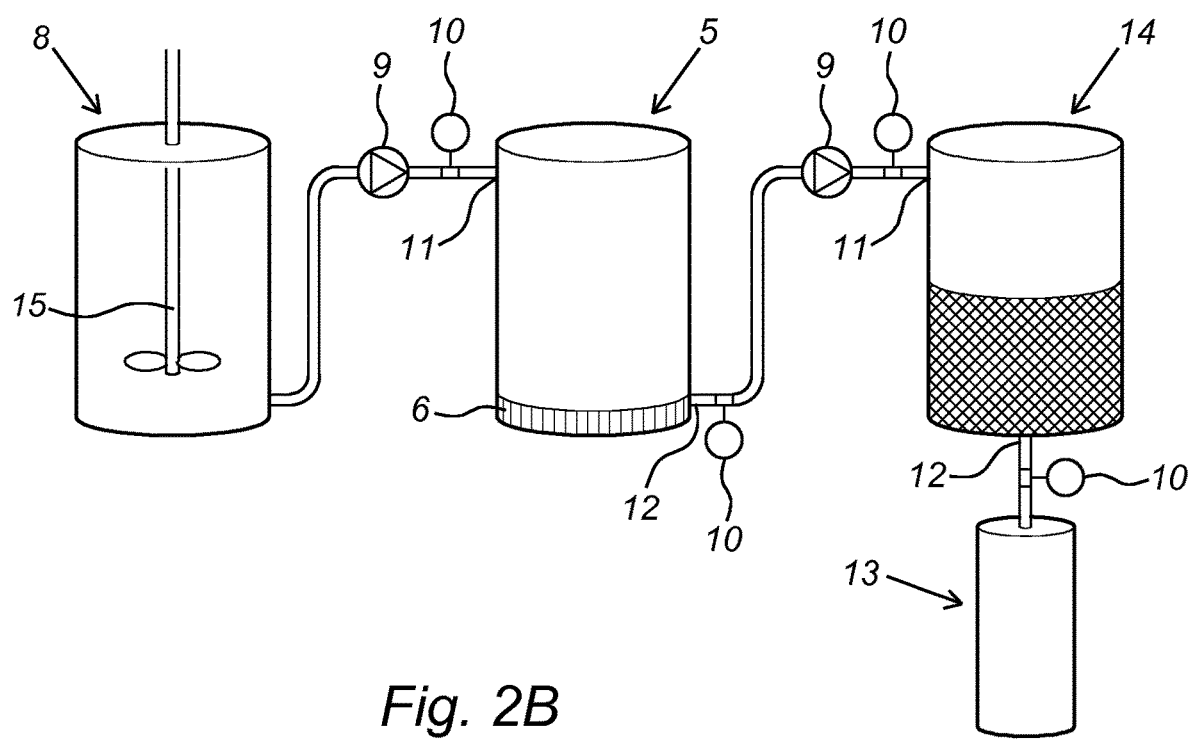

FIG. 2B Shows a Schematic Overview of a System for Clarifying a Cell Culture and Purifying Biomolecules of Interest, According to Embodiments of the Disclosure:

IgG1 Monoclonal Antibody Purification

One liter of fresh CHO cell culture unclarified harvest with viable cell density of $7.2 \cdot 10^6$ cells/ml and viability of 90% was kept at constant agitation in a vessel (8) for receiving a cell culture (such as an intermediate vessel, 3) downstream of a bioreactor (2) producing said culture). The cultured cells expressed IgG1 monoclonal antibody with a titer of approximately 0.5 g/L. Three harvest samples of 15 ml each were withdrawn to determine the wet cell weight (WCW) which was 38 g/L. The initial turbidity of the harvest was measured with a calibrated turbidimeter and was 1150 NTU.

The following compounds were added to the unclarified CHO cell culture in the vessel (8):
- 1% w/v of Allantoin (10 g per 1 liter of harvest),
- 0.45% v/v octanoic acid (4.5 ml per 1 liter of harvest), and
- 0.08% w/v of high molecular chitosan (0.8 g per 1 liter of harvest) with average molecular weight in the range of 300 kDa to 400 kDa.

The pH of the solution was adjusted to 5.30 using 1M acetic acid. The solution was agitated at 120 rpm at room temperature without letting the formed precipitates and/or floccules (1) to settle. After 45 minutes of constant agitation, 15.2 g of diatomaceous earth (DE, 4) of Celpure 300® grade were added to 1 L of solution (40% of the WCW which was determined experimentally prior to addition of the compounds). The formed solution was agitated for an additional 5 minutes. The solution was then subject to further processing as described below.

Afterwards, the vessel (8) that contained the solution was connected to a filtration vessel (5) that was made of polyethylene terephthalate housing and polyethylene membrane surface (6) with a pore distribution between 7 μm and 12 μm with a total surface area of 21 cm². The housing was impermeable for diatomaceous earth (4) of Celpure 300© particles and other large particulate material. The solution was kept under constant agitation and introduced into the filtration vessel (5) with a peristaltic pump (9) at a constant flowrate of 18 ml/min. A pressure sensor (10) was installed in the inlet (11) of the filtration vessel (5) and the flowrate was calculated using a reading of calibrated balances. The solution was filtered with the filtration vessel (5) within 48 minutes, which corresponds to an average flux of 511.9 LMH (liters per square meter per hour). The pressure measured at the inlet (11) of the filtration vessel (5) increased in a linear manner up to 0.68 bar by the end of filtration. The final filter capacity achieved was 409.5 l/m², and the turbidity of the filtrate was reduced from 1150 NTU to 17 NTU (this is a pool turbidity value; a perpetual decrease of filtrate turbidity was observed through duration of filtration). When the filtration ended, the DE cake or structure (7) was flushed with 70 ml of solution that contained 50 mM sodium acetate buffer, 125 mM sodium chloride and had pH 5.30. This was done to chase the product that is retained within the filter DE cake (7) and improve the recovery of the target molecule. The pool turbidity decreased down to 14.8 NTU after chasing the product with aid buffer.

The clarified harvest may optionally be processed with an additional second filtration vessel (14): a commercially available depth filter (Sartoclear P Caps DL20). The clarified harvest was filtered within 100 min with an overall flux of 206.4 LMH, a capacity at least 344 l/m² and at constant low pressure of 0.21 bar. The turbidity was reduced to 1.8 NTU. The depth filter was chased with the same buffer as the one used for DE filter cake (7) to recover the target product. The pH of the clarified harvest was adjusted to 7.0 with 2M TRIS base pH 9.5 and filtered with 0.22 μm filter before further processing.

The target molecule was captured from the clarified harvest in the purification unit (13) using three different affinity resins (CaptivA PriMab by Repligen, MabCapture A Select by Thermofischer Scientific and Amsphere A3 by JSR). The performance of the clarification method according to an embodiment of the disclosure was evaluated by measuring the CHO host cell proteins (HCP) content in affinity resins eluates using the generic CHO ELISA kit available from Cygnus Technologies. The HCP content in all eluates was consistent and was between 30 to 35 ppm.

IgG4 Monoclonal Antibody Purification

One liter of fresh CHO cell culture unclarified harvest with viable cell density of $3.2 \times 10^6$ cells/ml and viability of 81% was kept at constant agitation in a vessel (8) for producing a cell culture such as bioreactor (2). The cultured cells expressed IgG4 monoclonal antibody with a titer of 0.4 g/l and theoretical isoelectric point of 5.71. The WCW was 34 g/l. The initial turbidity of the harvest was measured was 528 NTU.

The following compounds were added to the unclarified CHO cell culture in the vessel (8):
- 1% w/v of Allantoin (10 g per 1 liter of harvest),
- 0.45% v/v octanoic acid (4.5 ml per 1 liter of harvest), and
- 0.075% v/v of poly (diallyldimethyl-ammonium chloride) (pDADMAC 0.075 mL per 1 liter of harvest) with average molecular weight in the range of 200 kDa to 350 kDa.

The pH of the solution was adjusted to 5.60±0.1 using 1M acetic acid and conductivity was kept without altering at 12±1 mS/cm. The solution was agitated at 150 rpm at room temperature without letting the formed precipitates and/or floccules (1) to settle. After 45 minutes of constant agitation, 13 g of diatomaceous earth (DE, 4) of Celpure 300© grade were added to 1 L of solution (approximately 40% of WCW). The formed solution was agitated for additional 15 minutes.

The vessel (8) that contained the solution was connected to a single use filtration vessel (5) that was made of a USP Class VI polyamide housing and its depth filter membrane of cellulose, a natural filter aid and a cationic strength agent, formed a surface (6) with a pore distribution between 10 μm to 30 μm with a total surface area of 20 cm². The surface (6) was impermeable for diatomaceous earth (4) of Celpure 300® particles and other large particulate material. The solution was kept under constant agitation and introduced into the filtration vessel (5) with a peristaltic pump (9) at a constant flowrate of 350 LMH. A pressure sensor (10) was installed in the inlet of the filtration vessel and the flow was monitored by reading of a calibrated balance. The pressure measured at the inlet of the filtration means increased in a linear manner up to 0.5 bar by the end of filtration. The final filter capacity achieved was 575.5 l/m2, and then the processing was stopped as all the cell culture harvest was clarified without reaching the pressure limits of the filtration vessel (5).

When the filtration ended, the formed cake (7) was flushed with 3 hold up volumes of equilibration buffer 50 mM sodium acetate buffer, 120 mM sodium chloride pH 5.60. The turbidity of clarified harvest pool was 1.2 NTU. The pH of the clarified harvest was adjusted to 7.0 with 2M TRIS base pH 9.5, and was then processed with a sterilizing grade second filtration vessel (14) made of polyethersulfone (PES) with pore size 0.5/0.2 µm. The sizing of the filter was based on Vmax test performed at constant pressure of 1 bar and the throughput volume achieved was more than 2,500 l/m2.

The target molecule was captured from the clarified harvest using a purification unit (13) comprising a Mabselect Sure LX affinity chromatography resin with 4 min residence time. The content of CHO host cell proteins (HCP) in the capture column eluate was measured using the generic CHO ELISA kit from Cygnus Technologies and was 42 ppm.

IgG1 Monoclonal Antibody Purification 0.5 L of fresh CHO cell culture unclarified harvest with viable cell density of $3.3 \times 10^6$ cells/ml and viability of 91% was kept at constant agitation in a vessel (8) for temporarily storing a cell culture (such as an intermediate vessel, 3) downstream of a bioreactor (2) producing said culture. The cultured cells expressed IgG1 monoclonal antibody with a titer of 0.44 g/L and theoretical isoelectric point of 8.61. The WCW was determined as described above and was 14.5 g/l.

The following compounds were added to the unclarified CHO cell culture in the vessel (8):
- 1% w/v of Allantoin (10 g per 1 liter of harvest),
- 0.45% v/v octanoic acid (4.5 ml per 1 liter of harvest), and
- 0.075% v/v of poly (diallyldimethyl-ammonium chloride) (pDADMAC 0.075 g per 1 liter of harvest) with average molecular weight in the range of 200 kDa to 350 kDa.

The pH of the solution was adjusted to 5.30±0.1 using 1M acetic acid and conductivity was kept at 12±1 mS/cm. The solution was agitated at 150 rpm at room temperature without settling the formed precipitates and/or floccules (1). After 30 minutes of constant agitation, 10 g/L of diatomaceous earth (DE, 4) of Celpure® 300 grade were added to the solution, which was then agitated for an additional 15 minutes.

The vessel (8) containing the solution was connected to a filtration vessel (5) with a housing made of USP Class VI polyamide and a depth filter membrane of cellulose, a natural filter aid and a cationic strength agent, which defined a surface (6) with a pore distribution between 10 µm to 30 µm with a total surface area of 20 cm². The surface (6) was impermeable for diatomaceous earth (4, DE) of Celpure 300© particles and other large particulate material.

The solution was kept under constant agitation and introduced into the filtration vessel (5) with a peristaltic pump (9) at a constant flowrate of 400 LMH. A pressure sensor (10) was installed in the inlet (11) of the filtration vessel (5) and the flow was monitored by reading of a calibrated balance. The pressure measured at the inlet (11) of the filtration vessel (5) increased in a linear manner up to 0.6 bar by the end of filtration. The final filter capacity achieved was 550 l/m2, and then the processing was stopped as all the cell culture harvest was clarified without reaching the pressure limits of the filtration vessel (5).

When the filtration ended, the formed cake (7) was flushed with 3 hold up volumes equilibration buffer 50 mM sodium acetate buffer, 120 mM sodium chloride pH 5.30 to chase the product that is retained within the filter cake (7) and improve the recovery. The turbidity of the clarified harvest pool was 1.1 NTU after processing. The pH of the clarified harvest was adjusted to 7.0 with 2M TRIS base pH 9.5, and then the clarified harvest was filtered with a second filtration vessel (14) consisting of a microfiltration vessel made of polyethersulfone (PES) with pore size 0.5/0.2 µm. The sizing of the filter was based on $V_{max}$ test performed at constant pressure of 1 bar and the throughput volume achieved was over 2,300 l/m2.

The target molecule (IgG1 monoclonal antibody) was captured from the clarified harvest in the purification unit (13) using a Mabselect Sure LX affinity chromatography resin with 4 min residence time. The content of CHO host cell proteins (HCP) in the capture column eluate was measured using the generic CHO ELISA kit from Cygnus Technologies and was 40 ppm.

IgG1 Monoclonal Antibody Purification 0.5 liter of fresh CHO cell culture unclarified harvest with viable cell density of $5.55 \times 10^6$ cells/ml and viability of 88% was kept at constant agitation in a vessel (8) for receiving a cell culture (such as an intermediate vessel, 3) downstream of a bioreactor (2) producing said culture. The cultured cells expressed IgG1 monoclonal antibody with a titer of 0.3 g/l and theoretical isoelectric point of 8.46.

The following compounds were added to the unclarified CHO cell culture in the vessel (8):
- 1% w/v of Allantoin (10 g per 1 liter of harvest),
- 0.45% v/v octanoic acid (4.5 ml per 1 liter of harvest), and
- 0.075% v/v of poly (diallyldimethyl-ammonium chloride) (pDADMAC, 0.075 g per 1 liter of harvest) with average molecular weight in the range of 200 kDa to 350 kDa.

The pH of the solution was adjusted to 5.30±0.1 using 1M acetic acid and conductivity was kept without altering at 12±1 mS/cm. The solution was agitated at 200 rpm at room temperature without letting the formed precipitates and/or floccules (1) to settle. After 30 minutes of constant agitation, diatomaceous earth (DE, 4) of Celpure 300® grade were added to solution to have a final concentration of DE equal to 15 g/l. The formed solution was agitated for an additional 15 minutes.

The vessel (8) that contained the solution was connected to a filtration vessel (5) with a housing made of USP Class VI polyamide and a depth filtration membrane of cellulose, a natural filter aid and a cationic strength agent, which defined a surface (6) with a pore distribution between 10 µm to 30 µm with a total surface area of 20 cm². The surface (6) was impermeable for diatomaceous earth (4) of Celpure 300® particles and other large particulate material.

The solution was kept under constant agitation and introduced into the filtration vessel (5) with a peristaltic pump (9) at a constant flowrate of 420 LMH. A pressure sensor (10) was installed in the inlet (11) of the filtration vessel (5) and the flow was monitored by reading of a calibrated balance. The pressure measured at the inlet (11) of the filtration vessel (5) increased in a linear manner up to 0.35 bar by the end of filtration. The final filter capacity achieved was 348.5 l/m², and then the processing was stopped as all the cell culture harvest was clarified without reaching the pressure limits of the filtration vessel (5).

When the filtration ended, the formed DE cake (7) was flushed with 3 hold up volumes of equilibration buffer 50 mM sodium acetate, 120 mM sodium chloride pH 5.30 to chase the product that is retained within the filter cake (7) and improve the recovery. The turbidity of the clarified harvest pool was 1.4 NTU.

The pH of the clarified harvest was adjusted to 7.0 with 2M TRIS base pH 9.5, and then the clarified harvest was filtered with a second filtration vessel (14) consisting of a microfiltration vessel made of polyethersulfone (PES) with pore sizes of 0.5/0.2 µm. The sizing of the micro filter was based on $V_{max}$ test performed at constant pressure of 1 bar, and the throughput achieved was more than 772 l/m2.

The target molecule (IgG1 monoclonal antibody) was captured from the clarified harvest using a purification unit (13) consisting of a Eshmuno A prepacked affinity column from Merck with 4 min residence time. The content of CHO host cell proteins (HCP) in capture column eluate was measured using the generic CHO ELISA kit from Cygnus Technologies and was 53 ppm.

IgG1 Monoclonal Antibody Purification 7.7 L of fresh CHO cell culture unclarified harvest with viable cell density of $3.3 \times 10^6$ cells/ml and viability of 91% was kept at constant agitation in a vessel (8) for receiving a cell culture (such as an intermediate vessel, 3) downstream of a bioreactor (2) producing said culture. The cultured cells expressed IgG1 monoclonal antibody with a titer of approximately 0.44 g/l and theoretical isoelectric point of 8.61. The WCW was determined as described above and was 14.5 g/L.

The following treatment was applied to the unclarified cell culture:

1% w/v of Allantoin (10 g per 1 liter of harvest),
0.45% v/v octanoic acid (4.5 ml per 1 liter of harvest), and
0.075% v/v poly (diallyldimethyl-ammonium chloride) (pDADMAC 0.075 g per 1 liter of harvest) with average molecular weight in the range of 200 kDa to 350 kDa.

The pH of the solution was adjusted to 5.30 using 1M acetic acid and conductivity was kept at 12±1 mS/cm. The solution was agitated at 150 rpm at room temperature without settling the formed precipitates and/or floccules (1). After 30 minutes of constant agitation, 10 g/l of diatomaceous earth (DE, 4) of Celpure 300© grade were added to the solution and the solution was agitated for an additional 15 minutes. The solution was then subjected to further processing as described below.

The vessel (8) that contained the solution was connected to a filtration vessel (5) with an external housing made of Polysulfone PSU/Stainless Steel and a surface (6) defined by a filter membrane with a pore size of 0.7 µm and a total surface area of 120 cm$^2$. The surface (6) was impermeable for diatomaceous earth (4) of Celpure 300© particles and other large particulate material.

The solution was kept under constant agitation and introduced into the filtration vessel (5) by a single-use centrifugal pump (9) with a flowrate of up to 1800 LMH in three separate cycles of equivalent volume. Pressure sensors (10) were installed in the inlet (11) and outlet (12) of the filtration vessel (5) to measure the differential pressure. The flow was monitored by an in-line flowmeter. The pressure measured at the inlet (11) of the filtration vessel (5) increased in a linear manner up to 0.65 bar by the end of filtration. A throughput of 642 l/m$^2$ was achieved and then the processing was stopped as all the cell culture harvest was clarified without reaching the pressure limits of the filtration vessel (5).

The DE cake (7) was flushed with 400 ml of equilibration buffer 50 mM sodium acetate buffer, 120 mM sodium chloride and had pH 5.30 to chase the product that is retained within the filter cake (7) and improve the recovery. The turbidity of clarified harvest pool 3 NTU.

The pH of the clarified harvest was adjusted to 7.0 with 2M TRIS-HCl pH 9.5 and then processed with a second filtration vessel (14) comprising a sterilizing grade filter made of polyethersulfone (PES) with pore size 0.2 µm.

The target molecule (IgG1 monoclonal antibody) was captured from the clarified harvest using a purification unit (13) comprising MAbSelect PrismA affinity chromatography medium with a 4 min residence time. The performance of the clarification using the method according to an embodiment of the disclosure was evaluated by measuring the CHO host cell proteins (HCP) content in affinity resin eluate using the generic CHO ELISA kit available from Cygnus Technologies. The content of CHO host cell proteins (HCP) in capture column eluate was measured using the generic CHO ELISA kit from Cygnus Technologies and was 72 ppm.

1. Floccules
2. Bioreactor
3. Intermediate vessel
4. Diatomaceous earth
5. Filtration vessel
6. Surface
7. Diatomaceous earth layer or cake
8. Vessel
9. Pump
10. Pressure sensor
11. Inlet
12. Outlet
13. Purification unit
14. Second filtration vessel
15. Mixer It is supposed that the disclosure is not restricted to any form of realization described previously and that some modifications can be added to the presented example without reappraisal of the appended claims.

The invention claimed is:

1. A method for cell culture clarification comprising:
    (a) adding at least three compounds to a cell culture harvest comprising at least one of an IgG1 monoclonal antibody and an IgG4 monoclonal antibody, wherein the at least three compounds facilitate the formation of floccules of solutes and/or particulates in said cell culture harvest, and wherein said cell culture harvest resides in a bioreactor or in an intermediate vessel downstream of a bioreactor producing said cell culture harvest, wherein the at least three compounds are chosen from the group consisting of fatty acids having 7 to 10 carbon atoms and derivatives thereof, ureides, and electropositive compounds;
    (b) adding an amount of diatomaceous earth (DE) to said cell culture harvest, wherein said added amount is from 20 to 60% of a measured cell culture wet cell weight;
    (c) agitating said cell culture harvest to form a harvest solution;
    (d) transferring the harvest solution to a filtration vessel comprising an inlet, an outlet, a reservoir and a support filter having a surface impermeable to DE and permitting said DE in said harvest solution to form a DE layer on said surface, wherein the harvest solution in the filtration vessel is not agitated;
    (e) filtering said harvest solution in the filtration vessel through said layer and support filter at a flowrate of 400 to 2000 liters per square meter per hour; and
    (f) collecting a clarified harvest from the outlet of the filtration vessel.

2. The method according to claim 1, wherein a pressure differential allows the formation of said DE layer on said surface.

3. The method according to claim 1, wherein in step (a) one or more of the fatty acids having 7 to 10 carbon atoms or derivatives thereof, one or more of the ureides which includes allantoin, and one or more of the electropositive compounds are added to the cell culture harvest.

4. The method according to claim 1, wherein said diatomaceous earth is added directly to said bioreactor.

5. The method according to claim 1, in which step (a) and (b) are simultaneous.

6. The method according to claim 1, wherein said amount of DE is added prior to step (a).

7. The method according to claim 1, wherein between 0.1% to 1.0% v/v of one or more of the fatty acids or derivatives thereof, between 0.5% to 3% w/v of one of more of the ureides including allantoin, and between 0.01% to 1% w/v of one or more of the electropositive compounds are added to the culture harvest.

8. The method according to claim 1, wherein the electropositive compounds are one of the compounds added to the cell culture harvest and are selected from the group consisting of electropositive polysaccharide, electropositive polymer, chitosan, a chitosan derivative, a synthetic polymer, pDADMAC, a cationic surfactant and any combination thereof.

9. The method according to claim 1, wherein said filtering step (e) comprises filtering the harvest solution at a flowrate of between 1000 and 2000 liters per square meter per hour.

10. The method according to claim 1, wherein the electropositive compounds include chitosan having a molecular weight of from 30 kDa to 1000 kDa, and the chitosan is one of the compounds added to the cell culture harvest.

11. The method according to claim 10, wherein the chitosan has a molecular weight of from 325 kDa to 375 kDa.

12. The method according to claim 1, wherein the inlet of the filtration vessel is above the outlet of the filtration vessel, and the support filter is located proximate the outlet and below the inlet so that the DE layer can be formed by gravity or pumping.

* * * * *